United States Patent [19]

Sawada et al.

[11] Patent Number: 5,068,454

[45] Date of Patent: Nov. 26, 1991

[54] POLYFLUOROALKANOYL PEROXIDE

[75] Inventors: Hideo Sawada, Tsukuba; Masaharu Nakayama, Tsuchiura, both of Japan

[73] Assignee: Nippon Oil & Fats Co. Ltd., Tokyo, Japan

[21] Appl. No.: 538,996

[22] Filed: Jun. 15, 1990

[30] Foreign Application Priority Data

Jun. 27, 1989 [JP] Japan .................................. 1-162609

[51] Int. Cl.$^5$ .......................................... C07C 409/00
[52] U.S. Cl. .................................................. 568/566
[58] Field of Search ......................................... 568/566

[56] References Cited

PUBLICATIONS

Chemical Abstracts 96:199049h Thermal Decomposition of Some Perfluoro-and Polyfluorodiacyl Peroxides, Zhao et al., J. Org. Chem. 1982, 47(11), 2009-13. Chemical Abstracts 107:237928z Crosslinked Fluorine-Containing Polymers, Takada, JP 62 59, 610, 1987.

*Primary Examiner*—Mary C. Lee
*Assistant Examiner*—Joseph K. McKane
*Attorney, Agent, or Firm*—Darby & Darby

[57] ABSTRACT

A polyfluoroalkanoyl peroxide has the formula (I)

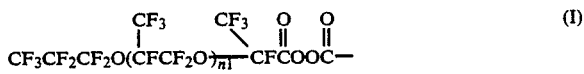
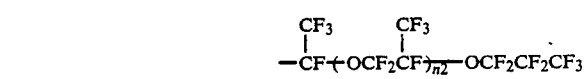

wherein $n_1$ and $n_2$ each represent an integer of 0 to 8 and $n_1$ plus $n_2$ is 1 or larger.

2 Claims, No Drawings

POLYFLUOROALKANOYL PEROXIDE

BACKGROUND OF THE INVENTION

This invention relates to a novel polyfluoroalkanoyl peroxide.

Conventionally, perfluoroalkanoyl peroxides are utilized as polymerization catalysts for fluorine monomers. In Japanese Laid-open Patent Publication No.10290/1974, for example, there is disclosed, as a catalyst for copolymerizing tetrafluoroethylene and hexafluoropropene, a perfluoroalkanoyl peroxide represented by the formula (II)

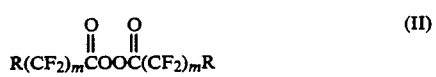

wherein R stands for a hydrogen atom or a fluorine atom and m stands for an integer of 2 to 24.

On the other hand, a report is made in the Journal of the Organic Chemistry, vol. 47, page 2009, 1982 as to a perfluoroalkanoyl peroxide represented by the formula

In general, long-chain perfluoroalkyl groups are known to be useful as polymerization initiators for the preparation of resins, since they are superior in water and oil repellency.

However, when preparing the peroxide of the above formula (II) in which the perfluoroalkyl group $R(CF_2)_m$ is a long-chain perfluoroalkyl group with m of 6 or more, since the long-chain perluoroalkyl group exhibits water and oil repellency, bubbling may be produced during the preparation, so that the yield of the product peroxide is significantly lowered.

Thus, there is a demand for polyfluoroalkanoyl peroxides having long-chain perfluoroalkyl groups which is novel and which may be produced easily industrially.

SUMMARY OF THE INVENTION

It is a principal object of the present invention to provide novel polyfluoroalkanoyl peroxides which are useful as polymerization catalysts for the preparation of resins and which are also useful as fluoroalkylating agents.

In accordance with the present invention, there is provided a polyfluoroalkanoyl peroxide having the formula (I)

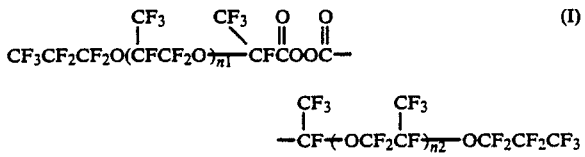

wherein $n_1$ and $n_2$ each represent an integer of 0 to 8 and $n_1$ plus $n_2$ is 1 or larger.

PREFERRED EMBODIMENTS OF THE INVENTION

The present invention will be explained hereinbelow in more detail.

The polyfluoroalkanoyl peroxide of the present invention is represented by the following formula (I)

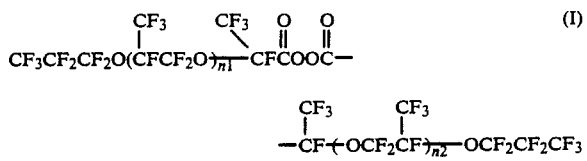

wherein $n_1$ and $n_2$ each represent an integer of 0 to 8 and $n_1$ plus $n_2$ is 1 or larger. If $n_1$ and/or $n_2$ is 9 or more, it becomes difficult to produce polyfluoroalkanoyl fluoride as a starting material.

The polyfluoroalkanoyl peroxides represented by the formula (I) may preferably include, for example, bis(-perfluoro-2,5-dimethyl-3,6-dioxanonanoyl)peroxide, bis(perfluoro-2,5,8-trimethyl-3,6,9-trioxadodecanoyl)-peroxide, bisperfluoro-2,5,8,11-tetramethyl-3,6,9,12-tetraoxa(pentadecanoyl)peroxide and bis(perfluoro-2,5,8,11,14-pentamethyl-3,6,9,12,15-pentaoxaoctadecanoyl)peroxide.

According to the present invention, the polyfluoroalkanoyl peroxide of the above formula (I) may be produced by a first method of reacting an acyl fluoride represented by the following formula (III)

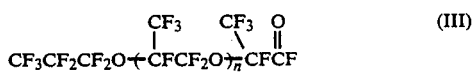

wherein n stands for an integer of 0 to 8, with hydrogen peroxide in the presence of a compound selected from the group consisting of sodium hydroxide, potassium hydroxide, sodium hydrogen carbonate, potassium hydrogen carbonate, sodium carbonate, potassium carbonate, and mixtures thereof, referred to hereinafter as component A, or a second method of reacting the acyl fluoride of the above formula (III) with a compound selected from the group consisting of sodium peroxide, potassium peroxide, barium peroxide and mixtures thereof, referred to hereinafter as component B.

In the above mentioned first method, a charging molar ratio of acyl fluoride, hydrogen peroxide and the component A may preferably be in the range of 1:0.3 to 20:0.3 to 10 and more preferably in the range of 1:0.5 to 10:0.5 to 7. In the second method, a charging molar ratio of acyl fluoride to the component B may preferably be 1:0.3 to 20 and more preferably 1:0.5 to 15. The charging molar ratios of the hydrogen peroxide and the component A to acyl fluoride in excess of 2 and 10, respectively, or the charging molar ratio of the component B to acyl fluoride in excess of 20 is not desirable since the yield of the produced polyfluoroalkanoyl peroxide is lowered. The above charging molar ratios less than 0.3 are also not desirable since the reaction time is prolonged and the product yield is lowered. The respective components A and B are preferably dissolved in water when introduced into the reaction system. The concentrations of the components A and B in the aqueous solutions are preferably each in the range of 1 to 60 wt. % and more preferably in the range of 5 to 30 wt. %. The above concentrations exceeding 60 wt. % are not desirable since the product yield is lowered, whereas the concentrations less than 1 wt. % are also not desirable since the reaction efficiency becomes so low that the methods cannot be applied industrially.

The reaction temperature and the reaction time duration for both the above described first and second methods are preferably −30° to +50° C. and 0.5 to 10 hours, respectively.

It is industrially preferred that the above reaction be carried out in an aliphatic solvent containing fluorine and/or chlorine atoms, such as, for example, 1, 1, 2-trichloro-1, 2, 2-trifluoroethane. The preferred reaction temperature at this time is in the range of −20° to +20° C.

The polyfluoroalkanoyl peroxide of the present invention is a novel compound and exhibits water and oil repellency, so that it is useful as a polymerization catalyst for electron-withdrawing monomers, such as tetrafluoroethylene, vinyl chloride, acrylonitrile or hexafluoropropene. It is also useful as a fluoroalkylating reagent for directly introducing a perfluoroalkyl group

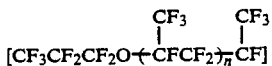

of the polyfluoroalkanoyl peroxide into an aromatic compound, such as benzene.

EXAMPLES OF THE INVENTION

The present invention will be explained in more detail with reference to Examples and Reference Examples. However, these Examples are given only for the sake of illustration and are not intended for limiting the invention.

EXAMPLE 1

Into a four-neck flask fitted with a stirrer, a thermometer and a dropping funnel were charged 3.37 g (0.06 mol) of potassium hydroxide and 28 g of water for dissolution. Then, after introducing 120 g of 1, 1, 2-trichloro-1, 2, 2-trifluoroethane under stirring to the solution, the resulting mixture was cooled to about −5° C., and 6.8 g (0.06 mol) of a 30 wt. % aqueous solution of hydrogen peroxide was added to the reaction mixture. A solution of 20 g (0.04 mol) of perfluoro-2, 5-dimethyl-3,6-dioxanonanoyl fluoride in 20 g of 1, 1, 2-trichloro-1, 2, 2-trifluoroethane was then added dropwise into the reaction mixture over 20 minutes at −5° to +5° C. After ageing for 60 minutes and separation of an organic layer, the reaction mixture was washed twice with 200 ml of water. The produced compound was analyzed by the iodometric method. The yield of the product was 93% (149 g), (the yield was based on the weight of the acyl fluoride). Upon analyses, the produced compound could be identified as bis(perfluoro-2, 5-dimethyl-3, 6-dioxanonanoyl)peroxide with a decomposition temperature of 16.41° C. at selected half-life value for 10 hours, an active oxygen percentage of 0.20% and a purity of 12.36%. The results of the analyses are shown below, while the thermal decomposition rate in the $CF_2ClCFCl_2$ solution of the above compound with the peroxide concentration of 0.02 mol/lit., are shown in Table 1.

Exact MASS: m/z: 990.1401, $C_{18}F_{34}O_8$: 990.1388 (calculated value)

$^{19}$F-NMR ($CF_2ClCFCl_2$+$CDCl_3$ δ ppm upfield from external $CF_3CO_2H$) 1.2 to 4.5 (26F), 50.4 (4F), 49.3 (2F), 60.3 (2F)

IR (cm$^{-1}$) 1825, 1870 (C=O), 1230 ($CF_2$), 1320, 1340 ($CF_3$)

TABLE 1

| Temperature (°C.) | $kd(S^{-1}) \times 10^5$ | Activation Energy |
|---|---|---|
| 10 | 0.82 | |
| 15 | 1.42 | 21 kcal/mol |
| 20 | 2.70 | |
| 25 | 5.36 | |

EXAMPLE 2

The reaction was carried out in the same way as in Example 1 except using perfluoro-2, 5, 8-trimethyl-3, 6, 9-trioxadodecanoyl fluoride in lieu of perfluoro-2, 5-dimethyl-3, 6-dioxanonanoyl fluoride. As a result of the analyses similar to those in Example 1, the produced compound could be identified as bis(perfluoro-2, 5, 8-trimethyl-3, 6, 9-trioxadodecanoyl) peroxide with a decomposition temperature of 15.8° C. at selected half-life value for 10 hours, an active oxygen percentage of 0.20% and a purity of 16.53%. The yield was 90% (145 g). The results of the analyses are shown as follows:

Exact MASS: m/z: 1322.1800, $C_{24}F_{46}O_{10}$: 1322.1844 (calculated value) $^{19}$F-NMR ($CF_2ClCFCl_2$+$CDCl_3$ δ ppm upfield from external $CF_3CO_2H$) 1.2 to 4.5 (36F), 50.4 (4F), 49.3 2F), 60.3 (4F)

IR (cm$^{-1}$) 1825, 1860 (C=O), 1230 ($CF_2$), 1335 ($CF_3$)

EXAMPLE 3

The reaction was carried out in the same way as in Example 1 except using perfluoro-2, 5, 8, 11-tetramethyl-3, 6, 9, 12-tetraoxapentadecanoyl fluoride in lieu of perfluoro-2, 5-dimethyl-3, 6-dioxanonanoyl fluoride. As a result of the analyses similar to those in Example 1, the produced compound could be identified as bis(perfluoro-2, 5, 8, 11-tetramethyl-3, 6, 9, 12-tetraoxapentadecanoyl) peroxide with a decomposition temperature of 15.0° C. at selected half-life value for 10 hours, an active oxygen percentage of 0.20% and a purity of 20.68%. The yield was 88% (141 g). The results of the analyses are shown as follows:

Exact MASS: m/z: 1654.2359, $C_{30}F_{58}O_{12}$: 1654.2300 (calculated value)

$^{19}$F-NMR ($CF_2ClCFCl_2$+$CDCl_3$ δ ppm upfield from external $CF_3CO_2H$) 1.2 to 4.5 (46F), 50.4 (4F), 49.3 (2F), 60.3 (6F)

IR (cm$^{-1}$) 1820, 1865 (C=O), 1225 ($CF_2$), 1340 ($CF_3$)

EXAMPLE 4

The reaction was carried out in the same way as in Example 1 except using perfluoro-2, 5, 8, 11, 14-pentamethyl-3, 6, 9, 12, 15-pentaoxaoctadecanoyl fluoride in lieu of perfluoro-2, 5-dimethyl-3, 6-dioxanonanoyl fluoride. As a result of the analyses similar to those in Example 1, the produced compound could be identified as bis(perfluoro-2, 5, 8, 11, 14-pentamethyl-3, 6, 9, 12, 15-pentaoxaoctadecanoyl) peroxide with a decomposition temperature of 14.3° C. at selected half-life value for 10 hours, an active oxygen percentage of 0.20% and a purity of 24.69%. The yield was 84% (138 g). The results of the analyses are shown as follows:

Exact MASS: m/z: 1986.3056, $C_{36}F_{70}O_{14}$, 1986.2756 (calculated value) $^{19}$F-NMR ($CF_2ClCFCl_2$+$CDCl_3$ δ ppm upfield from external $CF_3CO_2H$) 1.2 to 4.5 (56F), 50.4 (4F), 49.3 (2F), 60.3 (8F)

IR (cm$^{-1}$) 1820, 1870 (C=O), 1220 (CF$_2$), 1335 (CF$_3$)

Although the present invention has been described with reference to the specific examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A polyfluoroalkanoyl peroxide having the formula

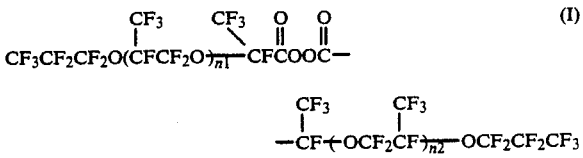

wherein $n_1$ and $n_2$ each represent an integer of 0 to 8 and $n_1$ plus $n_2$ is 1 or larger.

2. The polyfluoroalkanoyl peroxide according to claim 1 wherein the polyfluoroalkanoyl peroxide of the formula (I) is selected from the group consisting of bis(perfluoro-2, 5-dimethyl-3, 6-dioxanonanoyl)peroxide, bis(perfluoro-2, 5, 8-trimethyl-3, 6, 9-trioxadodecanoyl)period, bis(perfluoro-2, 5, 8, 11-tetramethyl-3, 6, 9, 12-tetraoxapentadecanoyl)peroxide and bis(perfluoro-2, 5, 8, 11, 14-pentamethyl-3, 6, 12, 15-pentaoxaoctadecanoyl)peroxide.

* * * * *